(12) United States Patent
Babaeizadeh et al.

(10) Patent No.: US 9,409,034 B2
(45) Date of Patent: Aug. 9, 2016

(54) SYSTEM, METHOD AND APPARATUS FOR ANALYZING CARDIAC RHYTHM DURING CPR

(71) Applicant: KONINKLIJKE PHILIPS N.V., Eindhoven (NL)

(72) Inventors: Saeed Babaeizadeh, Arlington, MA (US); Sophia Huai Zhou, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/404,040

(22) PCT Filed: May 29, 2013

(86) PCT No.: PCT/IB2013/054426
§ 371 (c)(1),
(2) Date: Nov. 26, 2014

(87) PCT Pub. No.: WO2013/179234
PCT Pub. Date: Dec. 5, 2013

(65) Prior Publication Data
US 2015/0165223 A1    Jun. 18, 2015

Related U.S. Application Data

(60) Provisional application No. 61/654,143, filed on Jun. 1, 2012.

(51) Int. Cl.
*A61N 1/00* (2006.01)
*A61N 1/39* (2006.01)
*A61B 5/00* (2006.01)
*A61B 5/04* (2006.01)
*A61B 5/0464* (2006.01)

(52) U.S. Cl.
CPC .......... *A61N 1/3987* (2013.01); *A61B 5/04012* (2013.01); *A61B 5/0464* (2013.01); *A61B 5/7217* (2013.01); *A61N 1/39* (2013.01); *A61N 1/3925* (2013.01)

(58) Field of Classification Search
USPC ........................................................ 607/7
See application file for complete search history.

(56) References Cited

U.S. PATENT DOCUMENTS 7,567,837 B2     7/2009   Well et al.
2006/0025824 A1  2/2006   Freeman et al.
(Continued)

FOREIGN PATENT DOCUMENTS

| GB | 2370880 A | 12/2004 |
| WO | 2006015348 A2 | 2/2006 |
| WO | 2011040929 A1 | 4/2011 |

OTHER PUBLICATIONS

Eilevstjonn, J. et al. "Feasibility of shock advice analysis during CPR through removal of CPR artefa from the human ECG". Resuscitation, May 2006; 61(2):131-41.

(Continued)

*Primary Examiner* — Nicole F Lavert

(57) ABSTRACT

A diagnostic medical device for identifying an arrhythmia treatable by a defibrillation shock includes a defibrillating a filter for filtering ECG data sets, a classifier and a electrotherapy circuit. The classifier is configured to classify filtered and unfiltered ECG data sets as a "shock" advice or a "no-shock" advice.

27 Claims, 8 Drawing Sheets

(56) References Cited

U.S. PATENT DOCUMENTS

| | | |
|---|---|---|
| 2006/0122648 A1 | 6/2006 | Elghazzawi et al. |
| 2008/0208070 A1 | 8/2008 | Snyder et al. |
| 2008/0312708 A1* | 12/2008 | Snyder .................. A61N 1/39 607/5 |
| 2011/0105930 A1 | 5/2011 | Thiagarajan et al. |
| 2011/0202100 A1 | 8/2011 | Tan et al. |

OTHER PUBLICATIONS

De Gauna, S.R. et al. "Filtering the cardiopulmonary resusictation artifact: Influence of the signal-to-noise ratio on the accuracy of the shock advice algorithm", Compuiting in Cardiology, 2010;37:681-684.

Ayala, U. et al. "An alternative to derive the instantaneous frequency of the chest compressions to suppress the CPR artifact". Computing in Cardiology, 2010; 37:545-548.

* cited by examiner

| Shock advisory algorithm advice | | Final decision |
|---|---|---|
| 1st Segment | 2nd Segment | |
| Shock / Shock | Shock / Shock | Arm |
| Shock / Shock | Shock / No-shock | Arm |
| Shock / No-shock | Shock / Shock | Arm |
| No-shock / Shock | No-shock / Shock | Arm |
| No-shock / Shock | No-shock / No-shock | Pause CPR |
| Shock / Shock | No-shock / No-shock | Pause CPR |
| No-shock / Shock | Shock / No-shock | Pause CPR |
| Shock / Shock | No-shock / Shock | Pause CPR |
| No-shock / Shock | Shock / Shock | Pause CPR |
| Any other combination | | Continue CPR |

FIG. 6

SYSTEM, METHOD AND APPARATUS FOR ANALYZING CARDIAC RHYTHM DURING CPR

This application is a national stage application under 35 U.S.C. §371 of International Application No. PCT/IB2013/054426 filed on May 29, 2013 and published in the English language on Dec. 5, 2013 as International Publication No. WO/2013/179234, which claims priority to U.S. Application No. 61/654,143 filed on Jun. 1, 2012, the entire disclosures of which are incorporated herein by reference.

The invention relates generally an improved method for monitoring a subject cardiac rhythm during the application of cardio-pulmonary resuscitation (CPR). More particularly, the invention relates to a medical device which incorporates an improved diagnostic algorithm that analyzes patient physiological data during CPR and determines if an electrotherapy shock is indicated. If the device is a defibrillator, the diagnostic algorithm provides user guidance and/or controls the device electrotherapy circuit based on the determination.

Sudden cardiac arrest (SCA) is a leading cause of death in the United States. In about 40% of sudden cardiac arrest (SCA) patients, the initial cardiac rhythm observed is ventricular fibrillation (VF). CPR is the protocol treatment for SCA, which consists of chest compressions and ventilations that provide circulation in the patient. Defibrillation is interposed between sessions of CPR in order to treat underlying VF. It is known that the probability of successful defibrillation diminishes as the interval between the end of CPR compressions and the delivery of a defibrillating shock increases. Conversely, shortening the interval between the last compression and the shock by even a few seconds can improve shock success (defibrillation and return of spontaneous circulation (ROSC)).

Furthermore, defibrillation does not terminate the underlying causes of VF even if it temporarily corrects the VF. Thus, the underlying causes may induce a recurrence of VF following defibrillation. This phenomenon is known as refibrillation. The present recommendation is to immediately resume chest compressions after the shock delivery for 2 minutes before analyzing the cardiac rhythm again. Some resuscitation thought leaders, however, believe that it is more beneficial to deliberately interrupt CPR early to deliver a shock aimed at correcting refibrillation.

Defibrillators deliver a high-voltage impulse to the heart in order to restore normal rhythm and contractile function in patients who are experiencing arrhythmia, such as VF or ventricular tachycardia (VT) that is not accompanied by spontaneous circulation. There are several classes of defibrillators, including manual defibrillators, implantable defibrillators, and automatic external defibrillators (AEDs). AEDs differ from manual defibrillators in that AEDs can automatically analyze the ECG rhythm to determine if defibrillation is necessary.

FIG. 1 is an illustration of a prior defibrillator 10 being applied by a user 12 to resuscitate a patient 14 suffering from cardiac arrest. In sudden cardiac arrest, the patient is stricken with a life threatening interruption to the normal heart rhythm, typically in the form of VF or VT that is not accompanied by spontaneous circulation (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient will die. Conversely, the quicker that circulation can be restored (via CPR and defibrillation) after the onset of VF, the better the chances that the patient 14 will survive the event. The defibrillator 10 may be in the form of an AED capable of being used by a first responder. The defibrillator 10 may also be in the form of a manual defibrillator for use by paramedics or other highly trained medical personnel.

Electrodes 16 are applied across the chest of the patient 14 by the user 12 in order to acquire an ECG signal from the patient's heart. The defibrillator 10 then analyzes the ECG signal for signs of arrhythmia. If VF is detected, the defibrillator 10 signals the user 12 that a shock is advised. After detecting VF or other shockable rhythm, the user 12 then presses a shock button on the defibrillator 10 to deliver defibrillation pulse to resuscitate the patient 14. Defibrillator 10 may also signal the user 12 via visual and audible prompts as to when to start and stop periods of CPR compressions.

In addition to detecting ECG voltages, defibrillator 10 independently measures the patient's transthoracic impedance via the patient electrodes 16 in order to adjust the parameters of the defibrillating shock accordingly. Variations in the impedance measurement can also be used to determine the extent of patient motion, such as that caused by CPR chest compressions. In other defibrillators (not shown), a separate CPR sensing device, such as an accelerometer or force sensor, may be used to provide an indication of ongoing CPR. An exemplary CPR sensing device is described in U.S. Pat. No. 7,108,665, entitled "CPR Chest Compression Monitor." If the defibrillator is integrated to an automated CPR machine, a compressions status signal from the machine may provide a CPR indication.

In prior art AEDs, the ECG analysis must be conducted during a non-CPR hands-off period because the electrical artifact induced by CPR-related motion makes the analysis algorithm unreliable. If the AED erroneously makes a false "shock" determination because of the artifact, it may enable the delivery of a shock potentially fatal to the patient. Thus, an adverse seconds-long interval between the end of CPR and the delivery of the shock impulse is necessary to provide for a clean analysis. For the same reasons, existing AED shock analysis algorithms are unable to detect and allow treatment for early refibrillation that occurs during CPR.

A number of methods have been developed in an attempt to determine an accurate ECG measurement during CPR compressions. U.S. Patent Publication 2011/0105930 A1 entitled "TRUE ECG MEASUREMENT DURING CARDIO PULMONARY RESUSCITATION BY ADAPTIVE PIECEWISE STITCHING ALGORITHM", for example, discloses using a filter to remove CPR artifact from the ECG. Similarly, International Publication WO 2011/040929 A1, entitled "DECIDING ON PATIENT ELECTRIC SHOCK THERAPY", describes a method for removing CPR artifact from an ECG prior to deciding as to whether to administer a shock to the patient. Another example, U.S. Pat. No. 7,567,837 entitled "ENHANCED RHYTHM IDENTIFICATION IN COMPRESSION CORRUPTED ECG" describes a method for identifying and removing CPR artifact by assuming that the artifact is a high amplitude signal, while the ECG is any low amplitude signal found between successive high amplitude signals. Finally, International Publication WO 2006/015348 A2 entitled "DETECTING ARTIFACT SIGNALS CAUSED BY CPR OR PATIENT MOTION" describes a method for detecting the presence of CPR artifact in an ECG signal, but no attempt is offered to obtain an accurate ECG from the contaminated signal. None of these prior art techniques provides a satisfactorily accurate ECG from which a shock decision could be made.

It is known that the fraction of patients who would benefit from a pause in CPR to confirm a shockable rhythm is small compared to the majority for whom continued CPR is beneficial. An algorithm that can determine a high likelihood of the presence of a shockable rhythm during CPR artifact (i.e. without pausing CPR) would allow distinguishing those who might benefit from an immediate shock without compromising resuscitation for the majority of patients.

What is needed therefore to address each of these deficiencies in the prior art is an improved method of analyzing an underlying cardiac rhythm in the presence of CPR.

In accordance with the principles of the present invention, a method for analyzing a cardiac rhythm in the presence of CPR artifact is described which accurately identifies the presence of an arrhythmia that is treatable by electrotherapy. The method comprises the steps of obtaining two or more time-sequential unfiltered ECG data sets, acquiring two or more time-sequential CPR reference signal data sets which correspond in time to the unfiltered ECG data sets, filtering the ECG data sets based on the acquiring step to obtain corresponding filtered ECG data sets, analyzing each of the filtered and unfiltered ECG data sets, classifying each of the filtered and unfiltered ECG data sets as a "shock" advice or a "no-shock" advice based on the analyzing step, and comparing the advices obtained in the classifying steps to decide whether or not to provide electrotherapy. The method may further use the result of the comparison step to issue an operational command to a medical device such as a defibrillator.

It is another object of the present invention to describe an improved method for analyzing a cardiac rhythm in the presence of CPR artifact. The improved method comprises the steps of obtaining two or more time-sequential unfiltered ECG data sets, acquiring two or more time-sequential CPR reference signal data sets which correspond in time to the unfiltered ECG data sets, filtering the ECG data sets based on the acquiring step to obtain corresponding filtered ECG data sets, analyzing each of the filtered and unfiltered ECG data sets, determining a reliability indicator for each of the filtered and unfiltered ECG data sets, classifying each of the filtered and unfiltered ECG data sets as a "shock" advice or a "no-shock" advice based on the analyzing step, and comparing the advices obtained in the classifying steps and the reliability indicator with decision criteria to determine whether or not to provide electrotherapy. The method may further use the result of the comparison step to issue an operational command to a medical device such as a defibrillator.

It is yet another object of the invention to describe a medical device which incorporates an improved ECG analysis method that accurately analyzes ECG in the presence of CPR artifact. The device may be a defibrillator or an AED. The device comprises a front end operable to obtain two or more time-sequential ECG data sets, an input operable to acquire two or more time-sequential CPR reference signal data sets which correspond in time to the time-sequential ECG data sets, a filter in communication with both of the front end and the input, the filter operable to obtain corresponding filtered ECG data sets, a shock classifier operable to analyze and classify each of the filtered and unfiltered ECG data sets as a "shock" advice or a "no-shock" advice, and a comparator operable to generate a decision output command based on the output of the shock classifier. The device may further comprise an output generator for issuing a command based on the decision output. The CPR reference signal input may be obtained from transthoracic impedance obtained from ECG electrodes, a CPR sensor, or from an automated CPR compressor device.

FIG. 6 is a truth table for decision criteria, corresponding to the FIG. 5 logic diagram.

Figure 1:
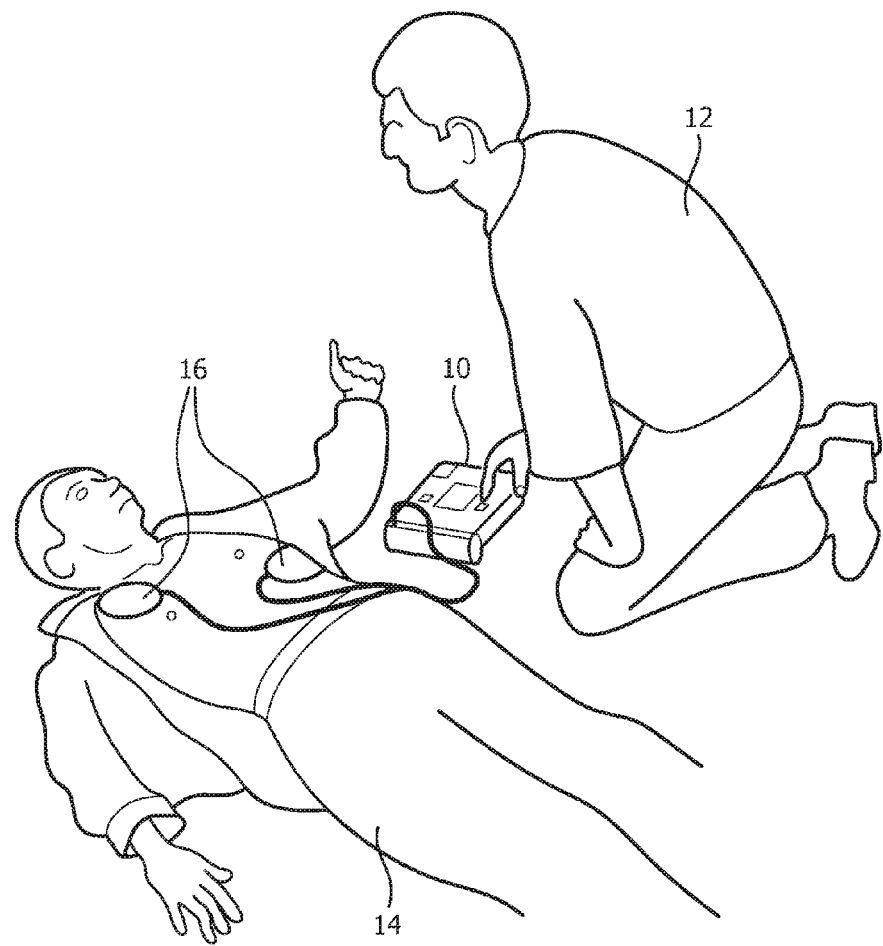
FIG. 1 is an illustration of a defibrillator which is in use with a patient suffering from cardiac arrest.
Figure 2:
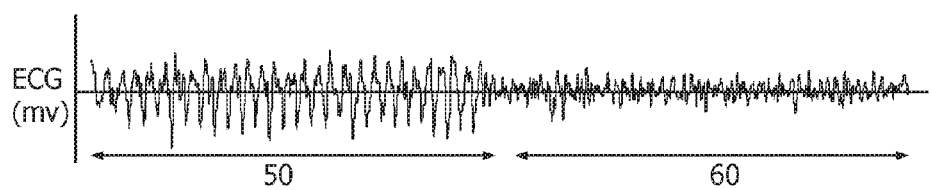
FIG. 2 illustrates a recording of a typical ECG, showing an ECG strip with CPR-induced artifact followed by an ECG strip without artifact.

Now turning to the figures, FIG. 2 illustrates an exemplary 23-second ECG strip from a subject patient whose underlying cardiac rhythm is VF. The first half (left hand side 50) of the waveform is recorded during CPR, and the second half (right hand side 60) is recorded after CPR has been paused, i.e. there is no chest compressions artifact on the ECG data. It can be seen that, during CPR at left hand side 50, the chest compression artifact induced on the ECG masks the underlying VF rhythm. A prior art shock advisory algorithm as applied to left hand side 50 might evaluate the CPR artifact as a regular ECG rhythm and erroneously determine that no shock is advised. This situation contrasts with an evaluation of the right hand side 60 waveform having no CPR artifact. There, a shock advisory algorithm can accurately detect the VF rhythm and properly advise a shock. Thus, FIG. 2 illustrates the problem with obtaining accurate ECG readings during CPR compressions that are ongoing during the rescue. FIG. 2 also illustrates that existing shock advisory algorithms would be unable to detect whether an ECG rhythm changes from a VF to a normal sinus rhythm or vice versa, i.e. refibrillation.

Figure 3:
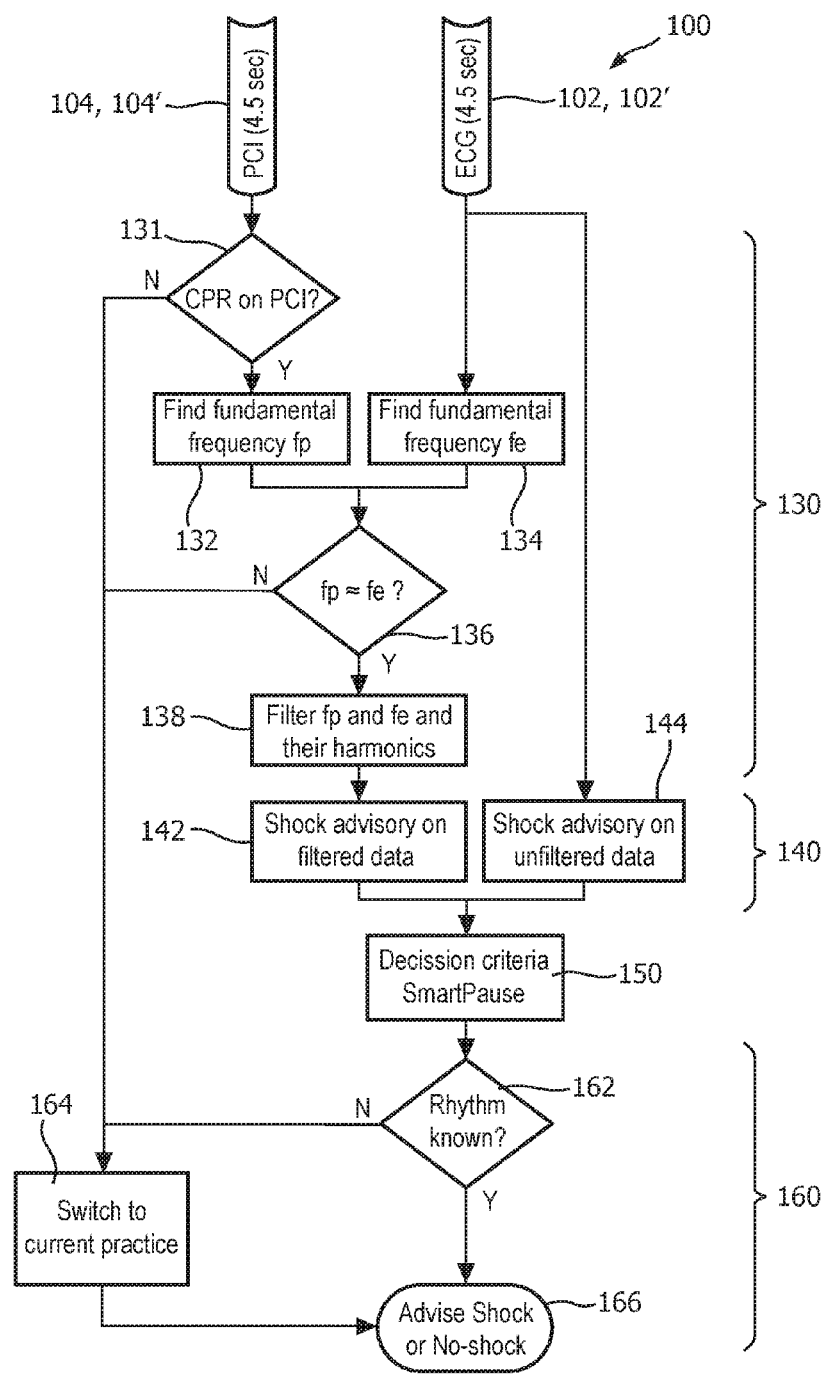
FIG. 3 is a basic flow diagram for a method of analyzing ECG during CPR.

The basic solution to the problem is illustrated by the flow chart of FIG. 3. The FIG. 3 method improves upon prior art methods by providing a shock advisory during CPR chest compressions by use of a technique that enables the analysis of the underlying cardiac rhythm during CPR. The technique allows for minimizing CPR hands-off intervals and increasing the likelihood of resuscitation success.

Shown in FIG. 3 are the steps to a novel method 100 for analyzing ECG during CPR. Method 100 combines a shock advisory algorithm at steps 142, 144 with an upstream filtering stage at step 130 and a downstream decision making stage at steps 150, 160. The basic method entails applying a shock advisory algorithm to sequences of both filtered and unfiltered ECG data. The resulting set of shock advisories, i.e. at least two pair, is compared to decision criteria to determine the proper output command guidance.

Figure 4A:
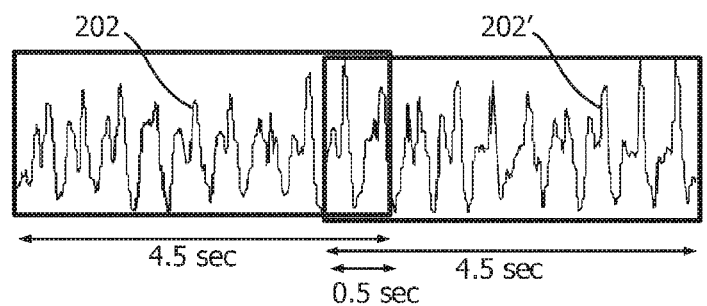
FIG. 4a illustrates a pair of time-sequenced ECG data sets according to a preferred embodiment of the invention.

The FIG. 3 method requires two types of data. The first is raw unfiltered ECG data, digitized and arranged into sets by segments of predetermined duration. FIG. 4a illustrates a preferred arrangement of ECG data, wherein a first unfiltered ECG data set 202 is 4.5 seconds long, and a second unfiltered ECG data set 202' overlaps with the first ECG data set 202 by 0.5 seconds. FIG. 3 illustrates the input of corresponding time-sequential ECG data sets 102, 102' into the method 100.

Figure 4B:
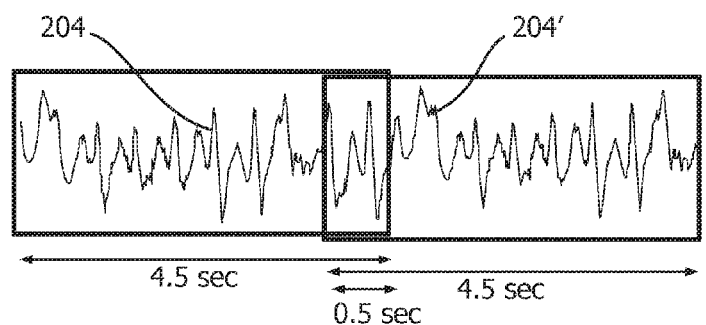
FIG. 4b illustrates a pair of time-sequenced CPR reference signal data sets, which also correspond in time to the FIG. 4a ECG data sets, according to a preferred embodiment of the invention.

The second type of data consists of CPR reference signal data, which is also arranged into sets by segments of predetermined duration. FIG. 4b illustrates a preferred arrangement of CPR data, wherein a first CPR reference signal data set 204 is 4.5 seconds long, and a second CPR reference signal data set 204' overlaps with the first CPR data set 204 by 0.5 seconds. Each CPR reference signal data set corresponds in time with the respective unfiltered ECG data set. FIG. 3 illustrates the input of corresponding time-sequential CPR reference signal data sets 104, 104' into the method 100.

FIG. 3 illustrates the required input of at least two time-sequential ECG data sets 102, 102' and at least two CPR reference signal data sets 104, 104' into the selective ECG filtering step 130 of method 100. A preliminary detecting chest compressions step 131 first determines if there is an indication of CPR artifact on either CPR reference signal data set. The output of step 131 is a Boolean indication of chest compression detection which is designed to be more sensitive than specific, and is based on evaluating variables in the CPR reference signal such as the range of amplitude and frequency, and the zero crossing rate.

If step 131 finds no indication of CPR on the reference signal, it may be preferable to analyze with a different shock advisory algorithm at step 164, thereby bypassing the balance of the inventive algorithm. An example alternate shock advisory algorithm is the PAS algorithm utilized in defibrillators manufactured by Koninklijke Philips, North America, Andover, Mass. The PAS algorithm is described in co-assigned U.S. Pat. No. 6,108,578, which is incorporated herein by reference.

If step 131 indicates CPR on the reference signal, then a confirming step of detecting chest compressions is applied to each of the ECG and CPR data sets. Fundamental frequencies are calculated using known techniques for each of the CPR data sets 104, 104' at step 132, and for each of the ECG data sets 102, 102' at step 134. Known techniques include discrete Fourier transform and Cepstrum analyses. The respective CPR and ECG data set fundamental frequencies Fp and Fe are then compared at step 136. If the fundamental frequencies are not comparable within a predetermined amount, CPR artifact on the ECG is not indicated, and further analysis is conducted with a different shock advisory algorithm at step 164, thereby bypassing the inventive algorithm. If the ECG and CPR frequencies are approximately equal, CPR artifact on the ECG is confirmed and the method continues at the filtering step 138.

The final filtering of CPR artifact from an ECG signal at step 138 generally follows one of the techniques that are known in the art. One preferred technique utilizes two Comb filters centered at Fp and Fe. Alternatively, the technique could employ a notch filter or some other sort of filter which filters a certain frequency and its harmonics. In addition, before filtering each set of data, "padding data" may be added to the beginning and end of the set to damp down the filtering artifact on the main evaluation window. The output of the filtering step 130 is thus a pair of time-sequential filtered ECG data sets comprising a first and second filtered ECG data set.

After the ECG segments are filtered at step 130, both sets of filtered and unfiltered ECG segments are analyzed and classified at step 140. First, a shock advisory algorithm analyzes each of the filtered and unfiltered ECG data sets at steps 142, 144 respectively. Several existing shock algorithms are suitable for use at steps 142, 144. One is the aforementioned PAS algorithm. Another is described in co-assigned U.S. Pat. No. 5,701,907 entitled "Electrocardiographic Waveform Monitoring Method and System."

The result of the analyzing steps 142, 144 is a set of four advices, each advice classifying each segment in each data set as either a shock advice or a no-shock advice. The shock advisory algorithms at steps 142, 144 may also classify an ECG data set as an "artifact" advice in the event that an ECG data set is too noisy for analysis.

Following the analyzing and classifying of the filtered and unfiltered ECG data sets, the set of advices are compared to decision criteria at step 150. The decision criteria are hereafter called SmartPause. Based on the particular combination of advices, SmartPause will output a decision of "arm", "continue CPR", or "pause CPR." If one or more of the advices is "artifact", SmartPause will preferably switch to an alternate method at step 162, which presumably would lead to a "do not touch the patient" prompt. Alternatively, SmartPause could directly issue a "pause CPR" decision, which would similarly lead to the same user prompt to discontinue touching the patient. In either case, the shock advisory algorithm will then have access to artifact-free ECGs. This technique for treating "artifact" advices, therefore, may not eliminate the CPR interruptions completely, but it would reduce the instances in which chest compressions are interrupted for AED operation.

The final step of method 100 is to automatically issue an operational command to the medical device at step 166 based on the comparing step 150. The example of FIG. 3 exemplifies the device as a defibrillator. The operational decision step 166 advises shock or no-shock as directed, which may further lead to automatically arming the defibrillator, issuing corresponding audible prompts such as verbal commands or beeps, and/or issuing corresponding visual prompts such as flashing lights or informational displays. In addition, the operational command may be to "pause CPR" in order to collect artifact-free ECGs, which would naturally lead to commands such as "do not touch the patient" and similar prompts. After CPR is discontinued, either as a result of a method 100 command or after the standard CPR pause period has timed-out, the shock advisory algorithm of the current practice, such as that indicated at step 164, would be used.

No device operational commands would be necessary in the event of a "continue CPR" decision. Alternatively, the device may issue informational status messages based on the decision in order to assure the user that the device is operating properly.

Figure 5:
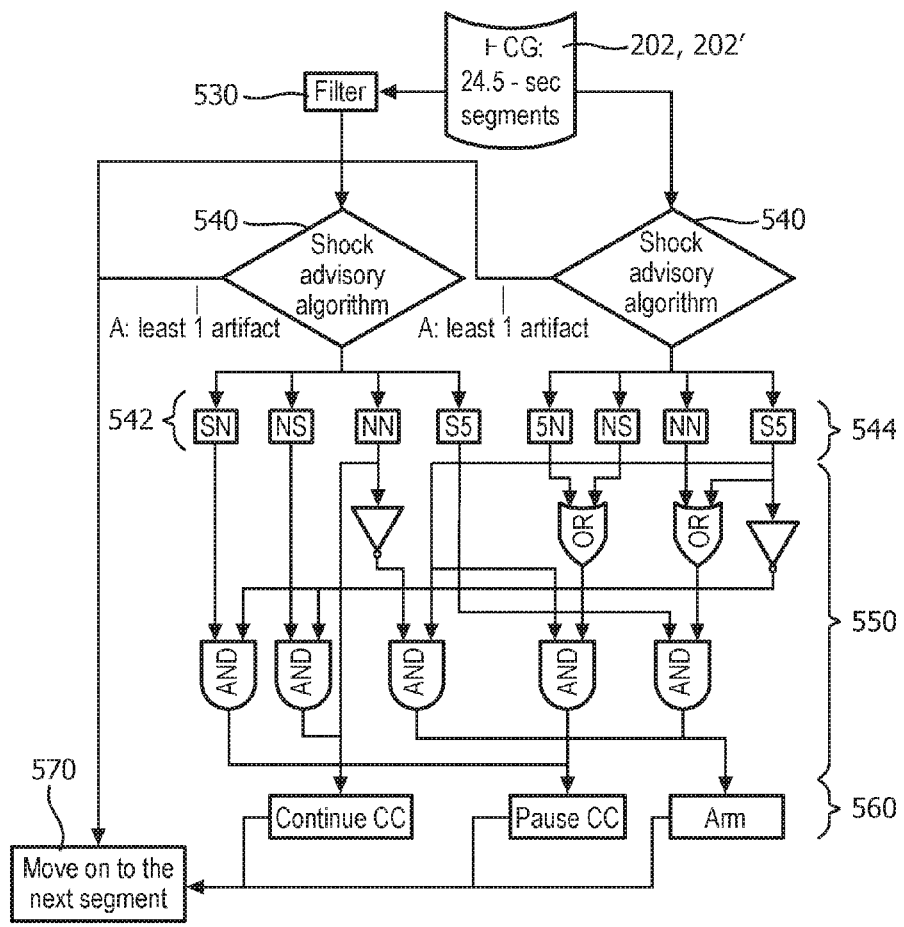
FIG. 5 illustrates a logic diagram for one embodiment of the inventive method, showing the interaction of a shock advisory algorithm, classifying criteria, and comparing criteria leading to an output decision.

Now turning to FIG. 5, a Boolean logic flow diagram for comparing advices and issuing an operational decision is illustrated. Similar to that discussed with reference to FIG. 3, two segments of unfiltered ECG data 202, 202' are applied to shock advisory algorithm 540. The unfiltered ECG data 202, 202' are also processed by filter 530, after which the filtered ECG data sets are applied to shock advisory algorithm 540. The output of each shock advisory algorithm 540 is two shock advices. A shock advice is designated by the letter "S." A no-shock advice is designated by the letter "N." All possible permutations 542 of advices for the filtered ECG data sets and all possible permutations 544 for the unfiltered ECG data sets are shown as outputs. Each particular combination of filtered and unfiltered ECG data set pairs flow through the Boolean logic diagram at 550 to arrive at a particular decision at 560. In this SmartPause decision criteria example, possible output decisions are "continue CPR", "pause CPR", and "arm". Following each decision, the process loops and repeats via loop step 570 with a new unfiltered ECG data set and the later of the previous unfiltered ECG data set. ECG data sets that are identified as having artifact are essentially discarded at the shock advisory algorithm stage 540, and the process similarly loops and repeats via loop step 570 with new unfiltered ECG data sets. Alternatively, an artifact decision could be directed to a "pause CPR" decision in order to collect artifact-free ECG.

The order of the shock advices matters in just one case. Referring to FIG. 5, it can be seen that an "NS" advice in a filtered ECG data set in combination with exactly one "S" advice in an unfiltered ECG data set results in "continue CPR." The result of an "SN" advice in a filtered ECG data set in combination with exactly one "S" advice in an unfiltered ECG data set results in "pause CPR." The reasoning for the different outcomes is as follows.

In the "NS" filtered ECG case, it is considered more prudent to merely await the results of the next unfiltered ECG advice pair than to issue an "arm" decision on just one shock advice. If the next filtered ECG segment advice is "Shock", then a "SS" advice pair results, leading to a proper "arm" decision. On the other hand, if the next filtered segment advice is "No-shock", then a "SN" advice pair results. The resulting decision to "pause CPR" enables the device to evaluate why the shock advisory algorithm advised shock and then changed the advice.

In the "SN" filtered ECG case, it is considered more prudent to immediately "pause CPR" in order to evaluate why the shock advisory algorithm changed an "S" advice to an "N" advice instead of waiting or proceeding to an "arm" decision. The "pause CPR" decision quickly leads to a hands-off situation having artifact-free ECG.

FIG. 6 illustrates a truth table for the SmartPause decision criteria corresponding to the FIG. 5 logic diagram. Each permutation of four advices 606, i.e. two time-sequential unfiltered ECG data set 604 advices and two corresponding time-sequential filtered ECG data set 602 advices, lead to one of a decision 608. In this case, the decisions are "arm", "pause CPR", or "continue CPR."

The inventors have discovered that the resulting SmartPause method output is more accurate in analyzing ECG during CPR than the prior art methods, which generally avoid analysis during CPR. SmartPause correctly issues "arm" operational commands to a sensitivity of 91% or higher and a specificity of 97% or higher. Sensitivity (Se) is the proportion of actual positives which are correctly identified as such (e.g. a correct arm decision based on the underlying ECG). Specificity (Sp) is the proportion of negatives which are correctly identified. In addition, the SmartPause method calls for an interruption of CPR (i.e. "pause CPR") only 10% of the time.

Another embodiment of the inventive method supplements the SmartPause decision criteria with a measure of confidence in the shock advisory advice. The measure of confidence is referred to as the reliability indicator. This alternative embodiment is dubbed SmartPause+.

Figure 7:
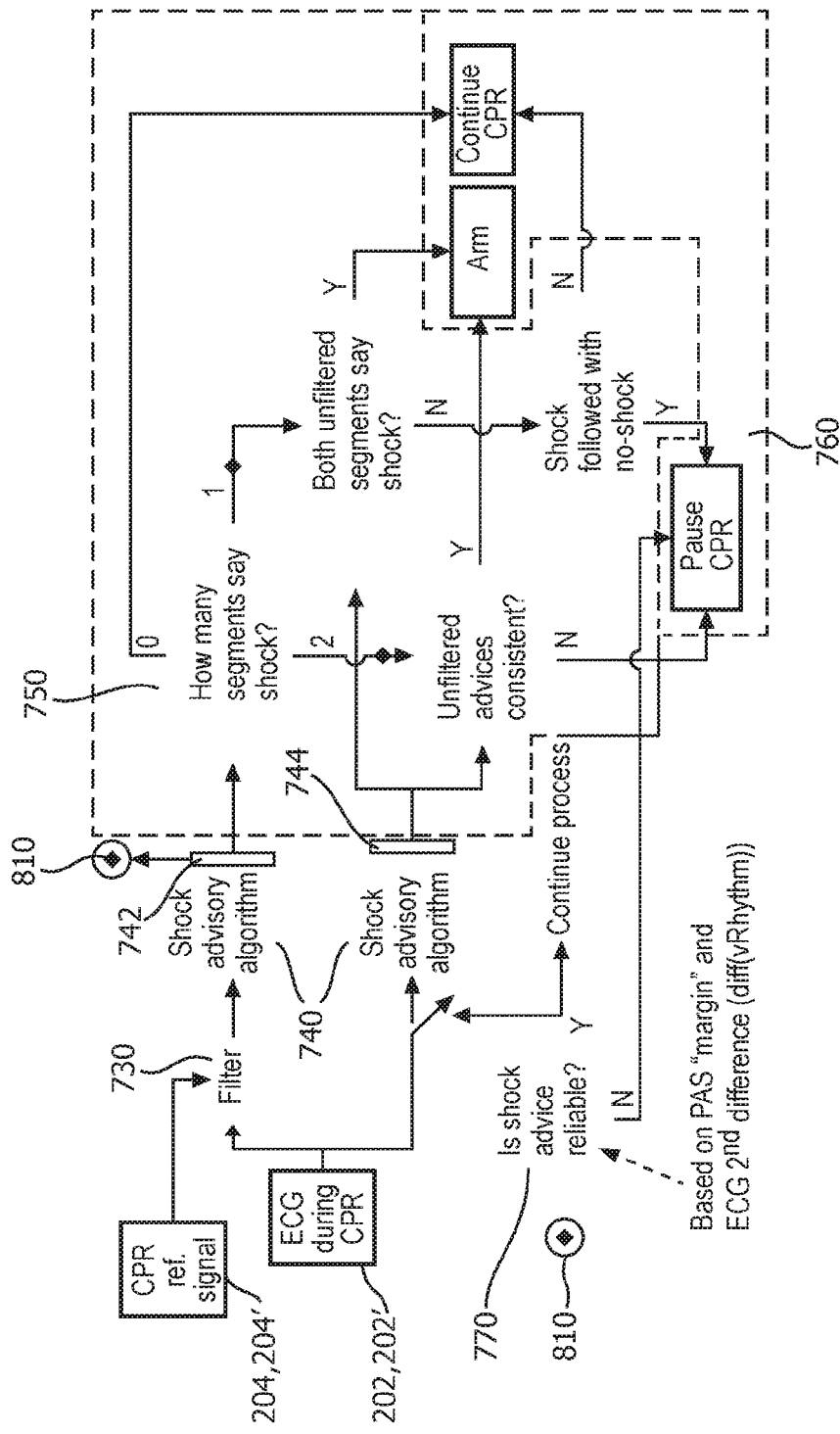
FIG. 7 illustrates a flow diagram according to an alternate embodiment of the inventive method, showing the interaction of a shock advisory algorithm, a reliability indicator, analyzing/classifying criteria, and comparing criteria leading to an output decision.

FIG. 7 illustrates a process flow diagram for the SmartPause+ method. The flow diagram uses many of the same major process steps as shown in FIG. 3 and the SmartPause logic diagram of FIG. 5. For example, similar inputs of first and second unfiltered ECG data sets 202, 202' and first and second CPR reference signal data sets 204, 204' are constructed in time-sequential segments as described in FIGS. 4a and 4b. Filter 730 processes the unfiltered ECG 202, 202' in the same manner as that described for filtering step 130 in FIG. 3. Both filtered and unfiltered ECG data sets are analyzed in analyzing step 740 by the shock advisory algorithm and classified in the classifying steps 742, 744 as "shock" advices or "no-shock" advices. The classified sets of advices are then compared to decision criteria logic in comparing step 750 to arrive at an operational decision step 760 that is issued to the subject medical device. Output decisions are "arm", "pause CPR", or "continue CPR."

The Smartpause+ method differs from the SmartPause method in two important ways. First, shock advisory algorithm 740 generates a reliability indicator 810 in addition to generating an advice. A preferred embodiment of reliability indicator 810 is a novel combination of a 'margin' to a shock advice and a measure of the 'shockability' of the underlying cardiac rhythm. Second, the reliability indicator 810 is used as an additional decision criterion in comparing step 750, which affects the output decision. Each of these differences is described below.

The 'margin' to a shock advice is an indication of how confident the shock advisory algorithm, such as the aforementioned PAS algorithm, is in its shock advice. 'Confidence' in this context means the margin between the measured characteristics of the ECG segment and the variables used in determining whether that ECG segment is shockable or not. One exemplary variable is heart rate. If PAS determines that the rhythm is shockable but the margin is relatively small, then PAS confidence is low. On the other hand if the margin is relatively large, then PAS confidence is high. Similarly, the margin indication can be applied to a non-shockable advice.

The measure of 'shockability' of a shockable VF ECG segment is determined in one of a number of ways. Techniques which have been used for VF wave analysis include measures based on VF amplitude and slope, VF frequency measures including wavelet decomposition, nonlinear dynamics methods, or a combination of these methods. One technique is described in detail in co-assigned U.S. Patent Publication Number 2008/0208070 A1, which is herein incorporated by reference. The preferred measure of 'shockability' is a function of the sum of absolute values of the second difference of the ECG signal in the segment.

Without undue experimentation, one of ordinary skill in the art can determine a desired weighting of the 'margin' and 'shockability' measures to arrive at the reliability indicator 810. The reliability measure is shown in FIG. 7 as applied to a filtered ECG data segment at step 740,742, but may alternatively be applied to an unfiltered ECG data segment at step 740,744. Preferably, the reliability indicator 810 is a binary measure of either "reliable" or "unreliable."

Returning to FIG. 7, a reliability assessment step 770 using the reliability indicator 810 determines how the SmartPause+ method will proceed. If the reliability indicator 810 is "reliable", SmartPause+ applies a comparing step 750 using the four advices obtained from the first and second filtered and unfiltered ECG data sets and the reliability indicator 810 as factors. If the reliability indicator 810 is 'unreliable', the SmartPause+ method bypasses comparing step 750 and proceeds directly to issuing an operational command of "pause CPR" at step 760. This ensures that at least one ECG data segment is reliable. Also, the bypassing saves computational time, and allows for the method to quickly obtain artifact-free ECG.

FIG. 7 illustrates the logic associated with comparing step 750, where a filled-in diamond indicates a 'reliable' reliability indicator for at least one filtered ECG data set. It can be seen there that at least one 'reliable' reliability indicator 810 is necessary, but not in itself sufficient, to enable an "arm" command at issuing step 760. In other aspects, the decision flow of comparing step 750 mirrors that in the aforedescribed logic diagram of FIG. 5, wherein the order of the shock advices matters.

Figure 8:
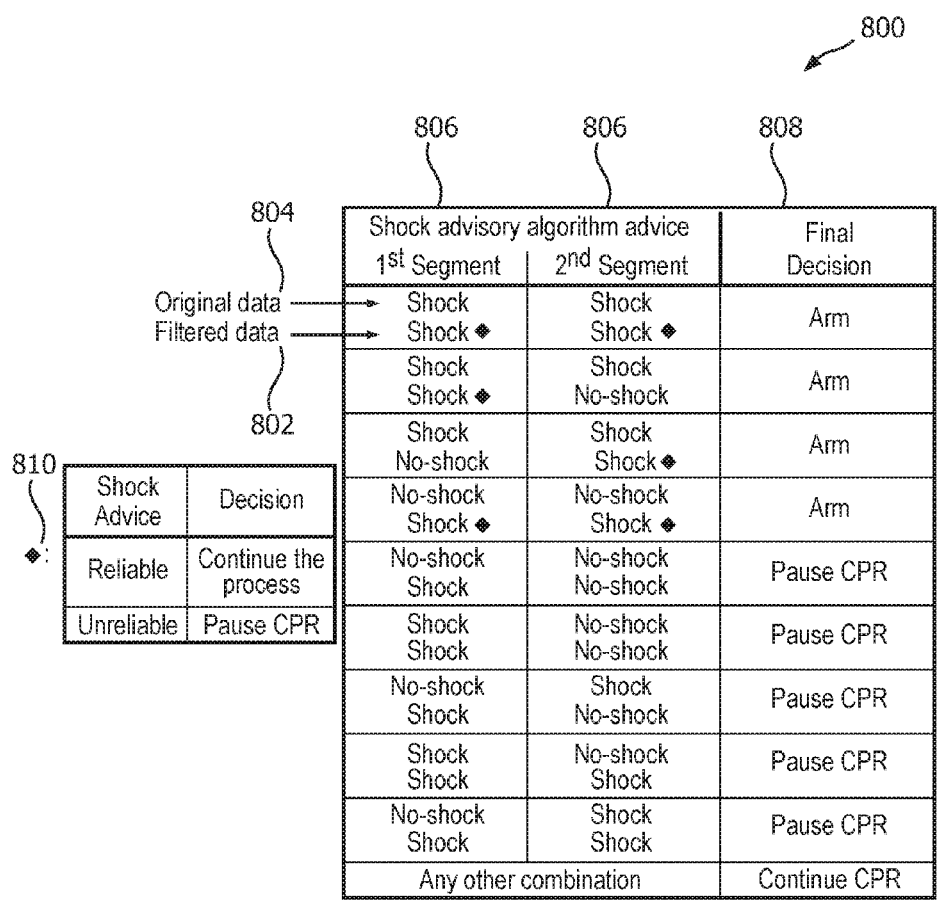
FIG. 8 is a truth table for decision criteria, corresponding generally to the FIG. 7 flow diagram.

FIG. 8 illustrates a truth table 800 for the SmartPause+ decision criteria corresponding to the FIG. 7 decision flow diagram. Each permutation of four advices 806, i.e. two time-sequential unfiltered ECG data set 804 advices and two corresponding time-sequential filtered ECG data set 802 advices, lead to one of an operational command 808. In this case, the operational command decisions are "arm", "pause CPR", or "continue CPR." It can be seen in FIG. 8 that a more restricted set of conditions are required in order to arrive at an "arm" operational command decision. In particular, at least one reliable shock indication 810 for a filtered ECG data set must exist in order to arm, regardless of the advices on the unfiltered ECG data sets.

The FIG. 8 truth table does not include decisions for every possible permutation of the four shock advices and reliability indicator, except for the "arm" decisions. It is understood that the FIG. 7 process flow diagram decisions take precedence over any discrepancy or omission in the FIG. 8 table.

The inventors have discovered that the resulting Smart-Pause+ method output is marginally more accurate in analyzing ECG during CPR than the aforedescribed SmartPause method. SmartPause+ correctly issues "arm" operational commands to a sensitivity of 92% or higher and a specificity of 99% or higher. The SmartPause method calls for an interruption of CPR (i.e. "pause CPR") only 14% of the time.

The inventive methods as described above are an improved clinical decision support tool intended for use in emergency care and resuscitation situations. The output of the tool can be used in several life-saving applications. First, by identifying a shockable rhythm prior to the end of the CPR protocol pause period, the analysis period following the pause period is unneeded. Quicker arming and shock delivery results, which improves the probability of resuscitation. The tool also enables the arming of a defibrillator during CPR protocol pause by interrupting chest compressions when a shockable rhythm is detected during CPR. Interrupting CPR for shock may be an effective treatment for the occurrence of refibrillation during the CPR pause. Third, the tool may accurately prompt a rescuer to stop CPR when an organized cardiac rhythm resumes during the CPR pause period. By discontinuing CPR chest compressions when they are no longer needed, the risk of CPR-induced injury is reduced. Finally, the tool may be used to monitor the quality and appropriateness of cardiopulmonary resuscitation in cardiac arrest events in both hospital and pre-hospital environments, i.e. the tool would act as a "CPR detector."

Figure 9:
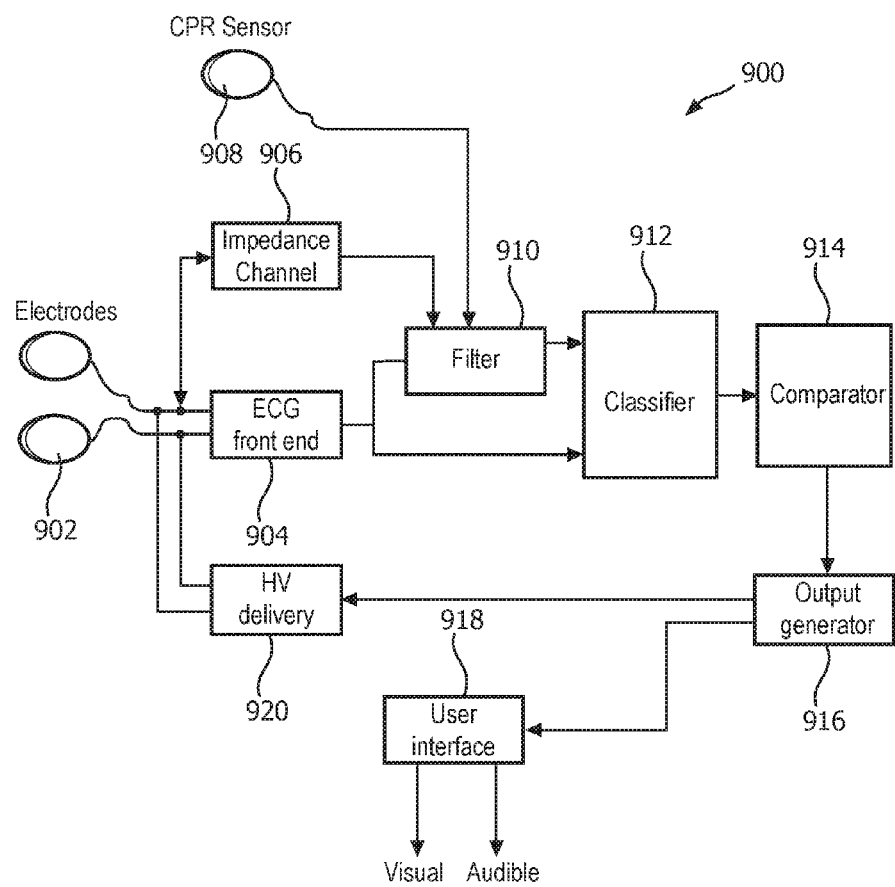
FIG. 9 is a block diagram of a medical device constructed in accordance with the principles of the present invention.

Now turning to FIG. 9, a medical device 900 is illustrated which incorporates a clinical decision support tool intended for use in emergency care and resuscitation situations. Device 900 enables an improved and more accurate analysis of ECG during CPR than that attempted by prior art devices.

Medical device 900 requires at least two inputs. Electrodes 902 which are attached to a subject patient detect the patient's ECG signal. The detected ECG signal is passed to an ECG front end 904, where the ECG is processed and digitized into a time-varying data stream. Front end 904 further groups the ECG data stream into time-sequential ECG data sets. In a preferred embodiment, the ECG data sets are 4.5 second segments which sequentially overlap by 0.5 seconds. Each raw, i.e. unfiltered, ECG data set is then output from front end 904 to a filter 910 and to a classifier circuit 912.

In addition, device 900 requires an input indicative of CPR compressions activity. The input can be obtained from one of a number of sources. Shown in FIG. 9 is a CPR sensor 908, which is typically a puck-like device that is placed between the patient's chest and the CPR-giver's hands. Sensors in the CPR sensor 908, such as force sensors and accelerometers, detect the CPR compressions and provide an input signal to device 900. Alternatively, CPR sensor 908 may be a compressions status signal that is obtained from an automated CPR machine, such as that currently sold as the AutoPulse™ Non-Invasive Cardiac Support Pump by Zoll Medical Corporation, Chelmsford, Mass. The automated CPR machine may provide an input indicative of the start of a CPR compression, for example.

A more preferred second input indicative of CPR is shown in FIG. 9 by the impedance channel 906. Many devices which monitor ECG also develop an impedance measurement across electrodes 902, in order to assess noise on the ECG signal, to detect patient motion, or to optimize electrotherapy parameters. Here, the impedance measurement is obtained at impedance channel 906 in order to provide the CPR input. This source of CPR input is advantageous because no additional hardware is required, saving rescue time and expense.

However it is detected, the input indicative of CPR compressions is provided to filter 910, where the input is initially digitized into a stream of time-varying CPR reference signals that indicate the frequency of chest compressions. Filter 910 further groups the digitized CPR signals into time-sequential CPR data sets. In a preferred embodiment, the CPR data sets are 4.5 second segments which sequentially overlap by 0.5 seconds. Each CPR data set corresponds in time to an ECG data set.

Filter 910 generates a sequence of filtered ECG data sets by applying the CPR reference signal data sets to each respective unfiltered ECG data set. The preferred and alternative methods of generating the filtered ECG data sets at filter 910 are as described previously. Each filtered ECG data set is output from filter 910 to classifier circuit 912.

Classifier circuit 912 applies an analysis algorithm to each filtered and unfiltered ECG data set, and classifies each data set as a "shock" or a "no-shock" rhythm, or "advice." If the data set cannot be classified, the set may optionally be classified as "artifact." The analysis algorithm is as described in the foregoing method discussion.

Classifier circuit 912 optionally incorporates a reliability analyzer that generates an indication of the reliability of each of the data set classifications. The reliability analysis algorithm is as described in the foregoing method discussion.

A comparator circuit 914 applies the classifications and optionally the reliability indications as obtained from classifier 912 to a decision matrix to generate a decision output command. The decision matrix corresponds to the logic flow and/or truth table arrangements as discussed in the aforedescribed inventive methods. The preferred output command is one of "arm", "continue CPR", or "pause CPR", depending on the output of the decision matrix.

Output generator 916 converts the decision output command from comparator 914 into an actionable issued command. If, for example, the decision output command is "arm", output generator 916 controls the device 900 to automatically begin arming a high voltage electrotherapy circuit, such as HV delivery circuit 920 of a defibrillator. Output generator 916 can also generate appropriate audible and visual indicators at user interface 918 to alert the rescuer of the actionable command. Decision output commands of "pause CPR" may cause output generator 916 to issue audible and visual indications to the rescuer to stop CPR. A decision output command of "continue CPR" may cause the output generator to issue no command at all.

Device 900 may be disposed as a stand-alone device, or may be integrated into another medical device system. For example, medical device 900 can be incorporated into a patient monitoring system for alerting medical personnel to changes in cardiac rhythm during CPR. Device 900 could also be integrated with a CPR assistance device which uses CPR sensor 908. It is contemplated that device 900 could also be used with an automated CPR machine, wherein the input to filter 910 could also be a machine compressions status signal and the output from the output generator could control changes in the machine operation. A preferred use for device 900 is of course as a component within a defibrillator or AED, wherein output generator 916 provides control for the arm function of a high voltage delivery circuit 920 based on the need to deliver a defibrillating shock, controls the user interface 918 to guide the user through a cardiac rescue, and optionally automatically delivers the shock through electrodes 902.

Minor modifications to the device as described above are encompassed within the scope of the invention. For example, several of the individual circuits shown in FIG. 9 may be integrated together into a single controller or processor in order to reduce complexity and space. Alternatively, some described function of the individual circuits may be performed by other of the circuits. A separate analog-digital conversion circuit, for example, could be dedicated to provide all of the pre-processing of ECG and CPR inputs. Variations in the nature and names of the outputs, which fulfill essentially the same user interface and device control objectives, also fall within the scope of the invention.

Table of Elements:

| Element Nr | Name |
| --- | --- |
| 10 | Defibrillator |
| 12 | User |
| 14 | Patient |
| 16 | Electrodes |
| 50 | ECG recording left hand side, with CPR artifact |
| 60 | ECG recording right hand side, without CPR artifact |
| 102, 102' | Obtaining first unfiltered ECG data set, second unfiltered ECG data set |
| 104, 104' | Obtaining first CPR reference signal data set, second CPR reference signal data set |
| 130 | Filtering step |
| 131 | Preliminary detecting chest compressions |
| 132 | Calculate CPR reference signal data fundamental frequency fp |
| 134 | Calculate unfiltered ECG data set fundamental frequency fe |
| 136 | Compare fp and fe |
| 138 | Filtering ECG data set |
| 140 | Analyzing and Classifying ECG data sets |
| 142 | Analyzing filtered ECG data set |
| 144 | Analyzing unfiltered ECG data set |
| 150 | Comparing the classified ECG data sets |
| 160 | Issuing operational command to the medical device. |
| 162 | Screening for known ECG rhythm |
| 164 | Switching to standard analyzing method |
| 166 | Changing device status |
| 202, 202' | first unfiltered ECG data set, second unfiltered ECG data set |
| 204, 204' | First CPR reference signal data set, second CPR reference signal data set |
| 530 | Filtering step |
| 540 | Analyzing step |
| 542 | Filtered ECG data set classifying step |
| 544 | Unfiltered ECG data set classifying step |
| 550 | Comparing step |
| 560 | Issuing operational command step |
| 570 | Looping process step |
| 600 | SmartPause truth table |
| 602 | Filtered classified ECG data |
| 604 | Unfiltered classified ECG data |
| 606 | Comparison sets |
| 608 | Operational Command |
| 730 | Filtering step |
| 740 | Analyzing step |
| 742 | Filtered ECG data set classifying step |
| 744 | Unfiltered ECG data set classifying step |
| 750 | Comparing step |
| 760 | Issuing operational command step |

-continued

Table of Elements:

| Element Nr | Name |
| --- | --- |
| 770 | Reliability assessment step |
| 800 | SmartPausePlus truth table |
| 802 | Filtered classified ECG data |
| 804 | Unfiltered classified ECG data |
| 806 | Comparison sets |
| 808 | Operational Command |
| 810 | Reliability indicator |
| 900 | Medical device |
| 902 | Electrodes |
| 904 | ECG front end |
| 906 | Impedance channel |
| 908 | CPR sensor |
| 910 | Filter |
| 912 | Classifier |
| 914 | Comparator |
| 916 | Output generator |
| 918 | User Interface |
| 920 | HV Delivery |

What is claimed is:

1. A medical device for diagnosing a cardiac rhythm during a performance of a cardio-pulmonary resuscitation (CPR) comprising:
a front end operable to obtain two or more time-sequential electrocardiogram (ECG) data sets comprised of a first unfiltered ECG data set and a second unfiltered ECG data set;
an input operable to acquire two or more time-sequential CPR reference signal data sets which correspond in time to the time-sequential ECG data sets;
a filter in communication with both of the front end and the input, operable to obtain a first filtered ECG data set and a second filtered ECG data set;
a shock classifier operable to classify each of the filtered and unfiltered ECG data sets as a "shock" advice or a "no-shock" advice;
a comparator operable to generate a decision based on the classified filtered and unfiltered ECG data sets;
an output generator for issuing an operational command based on the decision; and
a reliability analyzer operable to generate an indication of the reliability of each of the shock classifier advices based on the respective ECG data set;
wherein the comparator is further operable to generate the decision based on the reliability analyzer indications, and
wherein the reliability indicator indicates that the respective ECG data set is either reliable or unreliable, and wherein the issuing act issues an arm operational command only if at least one reliability indicator indicates a reliable ECG data set.

2. The medical device of claim 1, wherein the medical device is a defibrillator.

3. The medical device of claim 1, wherein the input is an impedance sensed across a pair of electrodes.

4. The medical device of claim 1, wherein the input is a CPR sensor comprising at least one of an accelerometer, a force sensor, or a compressions status signal from an automated CPR machine.

5. The medical device of claim 1, wherein the decision is one of the set comprising an arm decision, a pause CPR decision, or a continue CPR decision.

6. The medical device of claim 5, wherein the output generator issues a command comprising a user prompt to pause CPR based on the pause CPR decision.

7. The medical device of claim 1, further comprising:
a reliability analyzer operable to generate an indication of the reliability of each of the shock classifier advices based on the respective ECG data set;
wherein the comparator is further operable to generate the decision based on the reliability analyzer indications.

8. The medical device of claim 1, wherein the decision is accurate with a sensitivity of about 92% or higher and a specificity of about 99% or higher.

9. A method for controlling an operation of a medical device during a cardiac resuscitation of a subject, comprising the acts of:
obtaining two or more time-sequential electrocardiogram (ECG) data sets, comprised of a first unfiltered ECG data set and a second unfiltered ECG data set;
acquiring two or more time-sequential a cardio-pulmonary resuscitation (CPR) reference signal data sets which correspond in time to the time-sequential ECG data sets;
filtering the time-sequential ECG data sets based on the acquiring act to obtain a first filtered ECG data set and a second filtered ECG data set;
analyzing each of the filtered and unfiltered ECG data sets;
determining a reliability indicator for each of the filtered and unfiltered ECG data sets;
classifying each of the filtered and unfiltered ECG data sets as a "shock" advice or a "no-shock" advice based on the analyzing act;
comparing the advices and the reliability indicator to a decision criteria; and
issuing an operational command to the medical device based on the comparing act and the determining act,
wherein the reliability indicator indicates that the respective ECG data set is either reliable or unreliable, and wherein the issuing act issues an arm operational command only if at least one reliability indicator indicates a reliable ECG data set.

10. The method of claim 9, wherein the filtering act includes selecting from either of a first filtering protocol or a second filtering protocol to obtain the filtered ECG data sets, and wherein the selecting act selects based on a comparison of each of the time-sequential ECG data sets with the respective time-sequential CPR reference signal data sets.

11. The method of claim 10, wherein the second filtering protocol is a do nothing protocol.

12. The method of claim 10, wherein the comparison comprises comparing a fundamental frequency of each time-sequential ECG data set with a fundamental frequency of each time-sequential CPR reference signal data set.

13. The method of claim 9, wherein the classifying act further classifies each of the filtered and unfiltered ECG data sets as an "artifact" advice based on the analyzing act.

14. The method of claim 9, wherein the medical device is a defibrillator, and wherein the operational command is selected from the group of commands comprising an arm command, a pause CPR command, and a continue CPR command.

15. A system for controlling an operation of a medical device during a cardiac resuscitation of a subject, comprising:
one or more processors; and
a memory having stored thereon machine executable non-transitory instructions for execution by the processor, wherein execution of the machine executable non-transitory instructions causes the processor to:
obtain two or more time-sequential ECG data sets, comprised of a first unfiltered ECG data set and a second unfiltered ECG data set;
acquire two or more time-sequential CPR reference signal data sets which correspond in time to the time-sequential ECG data sets;
filter the acquired time-sequential ECG data sets to obtain a first filtered ECG data set and a second filtered ECG data set;
analyze each of the filtered and unfiltered ECG data sets;
determining a reliability indicator for each of the filtered and unfiltered ECG data sets;
classify each of the analyzed filtered and unfiltered ECG data sets as a "shock" advice or a "no-shock";
compare the classified advices;
automatically issue an operational command to the medical device based on the comparison,
wherein the reliability indicator indicates that the respective ECG data set is either reliable or unreliable, and wherein the issuing act issues an arm operational command only if at least one reliability indicator indicates a reliable ECG data set.

16. The system of claim 15, wherein execution of the machine executable non-transitory instructions further causes the processor to perform a selection from either of a first filtering protocol or a second filtering protocol to obtain the filtered ECG data sets, and wherein the selection is based on a comparison of each of the time-sequential ECG data sets with the respective time-sequential CPR reference signal data sets.

17. The system of claim 16, wherein the second filtering protocol is a do nothing protocol, and wherein the comparison comprises comparing a fundamental frequency of each time-sequential ECG data set with a fundamental frequency of each time-sequential CPR reference signal data set.

18. The system of claim 15, wherein execution of the machine executable non-transitory instructions further causes the processor to further classify each of the analyzed filtered and unfiltered ECG data sets as an "artifact" advice.

19. The system of claim 15, wherein the device is a defibrillator, and further wherein the operational command is selected from the group of commands comprising an arm command, a pause CPR command, and a continue CPR command.

20. The medical device of claim 1, wherein the indication of reliability by the reliability analyzer is a combination of a margin to each of the shock classifier advices and a measure of shockability of the cardiac rhythm.

21. A medical device for diagnosing a cardiac rhythm during a performance of a cardio-pulmonary resuscitation (CPR) comprising:
a front end operable to obtain two or more time-sequential electrocardiogram (ECG) data sets comprised of a first unfiltered ECG data set and a second unfiltered ECG data set;
an input operable to acquire two or more time-sequential CPR reference signal data sets which correspond in time to the time-sequential ECG data sets;
a filter in communication with both of the front end and the input, operable to obtain a first filtered ECG data set and a second filtered ECG data set; and
a processor configured to perform a selection of either a first filtering protocol or a second filtering protocol to obtain the first and second filtered ECG data sets, and wherein the selection is based on a comparison of each of the time-sequential ECG data sets with the respective time-sequential CPR reference signal data sets.

22. The medical device of claim 21, wherein the comparison comprises comparing a fundamental frequency of each time-sequential ECG data set with a fundamental frequency of each time-sequential CPR reference signal data set, and wherein the first filtering protocol is selected when a CPR artifact is present, the CPR artifact being present when the fundamental frequency of the time-sequential ECG data sets and the fundamental frequency of the respective time-sequential CPR reference signal data sets are equal.

23. The medical device of claim 21, further comprising:
a shock classifier operable to classify each of the filtered and unfiltered ECG data sets as a "shock" advice, a "no-shock" advice or an "artifact" advice;
a comparator operable to generate a decision based on the classified filtered and unfiltered ECG data sets; and
an output generator for issuing an operational command based on the decision,
wherein the shock classifier and the comparator are operable without pausing CPR.

24. The medical device of claim 21, further comprising a chest compressions detector configured to detect an indication of a CPR artifact on each time-sequential CPR reference signal data set,
wherein the chest compressions detector is operable based on evaluating variables in the time-sequential CPR reference signal data sets, the variables being at least one of a range of amplitude, a range of frequency and a zero crossing rate, and
wherein an analysis of the time-sequential ECG data sets and the first and second filtered ECG data sets are performed by the processor during a presence of the CPR artifact.

25. The medical device of claim 21, wherein the processor is configured to perform the selection during the performance of CPR.

26. The medical device of claim 21, wherein the two or more time-sequential ECG data sets at least partially overlap in time with each other, and wherein the two or more time-sequential CPR reference signal data sets at least partially overlap in time with each other.

27. The medical device of claim 21, wherein padding data is added to the first and second unfiltered ECG data sets prior to the filter obtaining the first and second filtered ECG data sets.

* * * * *